United States Patent [19]

Hamdy et al.

[11] Patent Number: 5,041,370

[45] Date of Patent: Aug. 20, 1991

[54] PSEUDORABIES VIRUS (PRV) GENE, HOST CELL, METHOD FOR DETECTING ANIMALS INFECTED WITH PSEUDORABIES VIRUS, AND KIT THEREFOR

[75] Inventors: deceased Hamdy; by Heide M Hamdy, heir, late of Portage; Roger J. Brideau, Portage; Leonard E. Post, Oshtemo Township, Kalamazoo County; Thomas J. Rea, Kalamazoo, all of Mich.; James G. Timmins, Naperville, Ill.; Carmine C. Marchioli, Ypsilanti, Mich.

[73] Assignee: The Upjohn Company, Kalamazoo, Mich.

[21] Appl. No.: 853,087

[22] Filed: Apr. 17, 1986

Related U.S. Application Data

[63] Continuation-in-part of Ser. No. 606,103, May 2, 1984, abandoned, and a continuation-in-part of Ser. No. 606,307, May 2, 1984, abandoned.

[51] Int. Cl.$^5$ ........................................... G01N 33/569
[52] U.S. Cl. ........................................ 435/5; 435/6; 435/7.1; 435/69.1; 435/69.3; 435/70.1; 435/70.3; 435/240.2; 435/252.3; 435/252.33; 530/387; 530/395; 530/826; 530/829; 536/27; 935/12; 935/24; 935/28; 935/29
[58] Field of Search .......................................... 435/5–7, 435/68, 70, 172.3, 235, 240, 317, 253, 255, 243, 810, 7.1, 69.1, 69.3, 70.1, 70.3, 235.1, 240.2, 317.1, 252.3, 252.33; 436/514, 515, 807–809; 530/387, 395, 826, 829; 536/27; 935/12, 24, 28, 29

[56] References Cited

U.S. PATENT DOCUMENTS 4,393,201 7/1983 Curtis .................................... 536/37
4,562,147 12/1985 Joo .................................. 436/514 X

FOREIGN PATENT DOCUMENTS 0133200 2/1985 European Pat. Off.
162738 11/1985 European Pat. Off. ............ 435/235

OTHER PUBLICATIONS

K. B. Platt, et al., "Evaluation of a Diagnostic Antigen for the Detection of Aujeszky's Disease Virus-Infected Subunit-Vaccinated Pigs", Veterinary Microbiology, 11, pp. 25-40 (1986).
U.S. Ser. No. 760,130 filed 7/29/85, L. E. Post and D. R. Thomsen.
U.S. Ser. No. 049,865 filed 3/27/87, L. E. Post and D. R. Thomsen.
D. Todd, et al., "Enzyme-linked immunosorbent assay for detecting antibodies to Aujeszky's disease virus in pigs", The Veterinary Record, pp. 534–537 (1981).
F. Moutou et al., "Application of an enzyme linked immunosorbent assay for diagnosis of Aujeszky's disease in swine", Veterinary Record (1978) 102.264.
Rea et al., J. Virology, 54(1): 21–29 (1985).
T. Ben-Porat and A. S. Kaplan, "Synthesis of Proteins in Cells Infected with Herpesvirus, V. Viral Glycoproteins", Virology, 41, pp. 265–273 (1970).
A. S. Kaplan and T. Ben-Porat, "Synthesis of Proteins in Cells Infected with Herpesvirus, VI. Characterization of the Proteins of the Viral Membrane", Proc. Natl. Acad. Sci., USA, 66, pp. 799–806 (1970).
A. S. Kaplan, et al., "Excretion of Specific Glycoproteins by Cells Infected with Herpes Simplex Virus, Types 1 and 2", Progr. Med. Virol., vol. 21, pp. 1–12 (1975).
R. E. Randall and R. W. Honess, "Proteins of Herpesvirus Saimiri: Identification of Two Virus Polypeptides Released into the Culture Medium of Productively Infected Cells", J. Gen Virol., 51, pp. 445–449 (1980).
D. Van Zaane, et al., "Molecular-Biological Characterization of Marek's Disease Virus, I. Identification of Virus-Specific Polypeptides in Infected Cells", Virology, 121, pp. 116–132 (1982).
J. S. Erickson and A. S. Kaplan, "Synthesis of Proteins in Cells Infected with Herpesvirus, IX. Sulfated Proteins", Virology, 55, pp. 94–102 (1973).

Primary Examiner—Robert J. Hill
Attorney, Agent, or Firm—Paul J. Koivuniemi

[57] ABSTRACT

The present invention provides a recombinant DNA sequence encoding the pseudorabies virus (PRV) glycoprotein gX, host cells transformed by said DNA sequence, the gX polypeptide, and methods and kits for detecting animals infected with PRV.

11 Claims, 5 Drawing Sheets

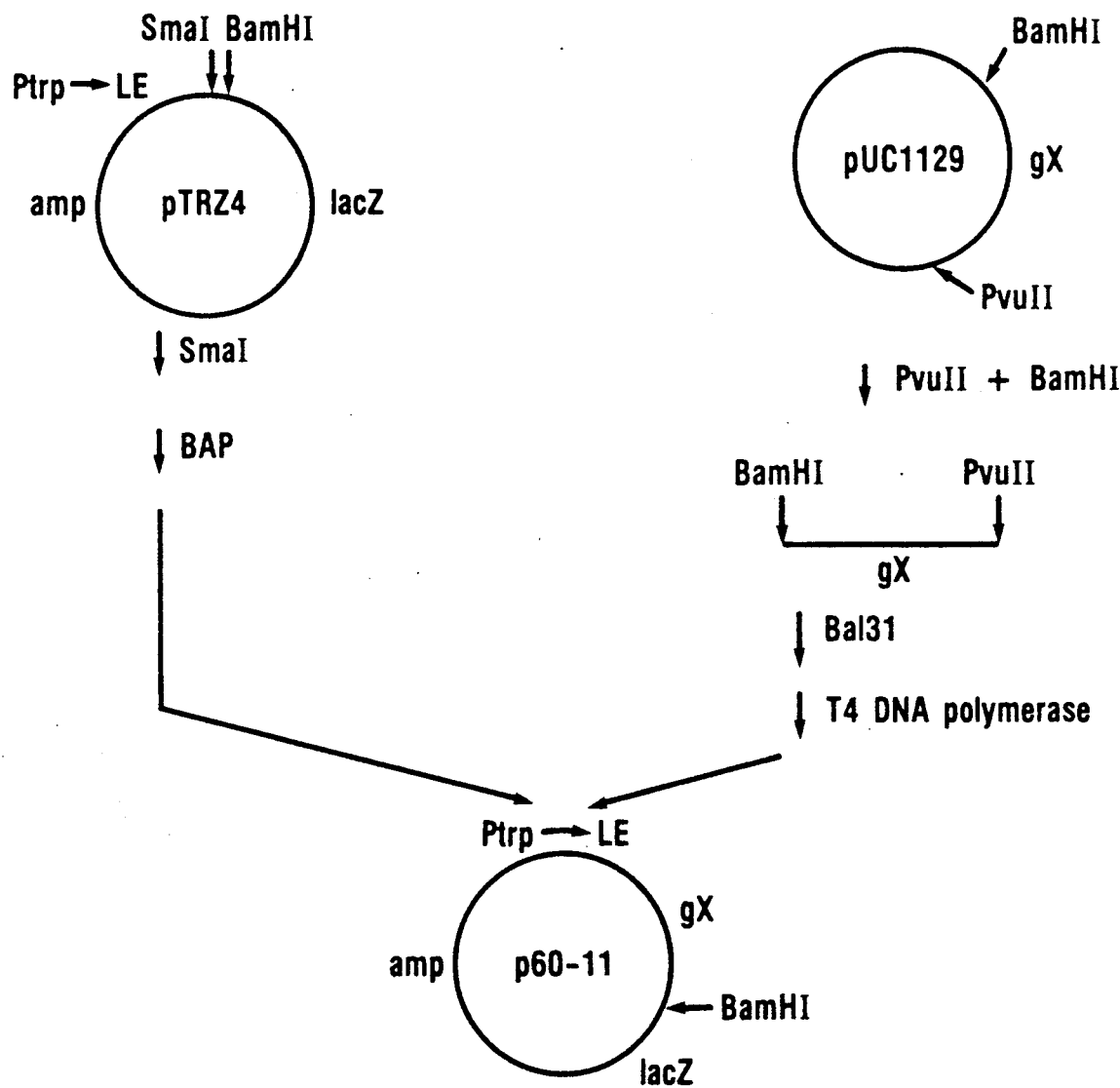
Figure 3. Construction of p60-11

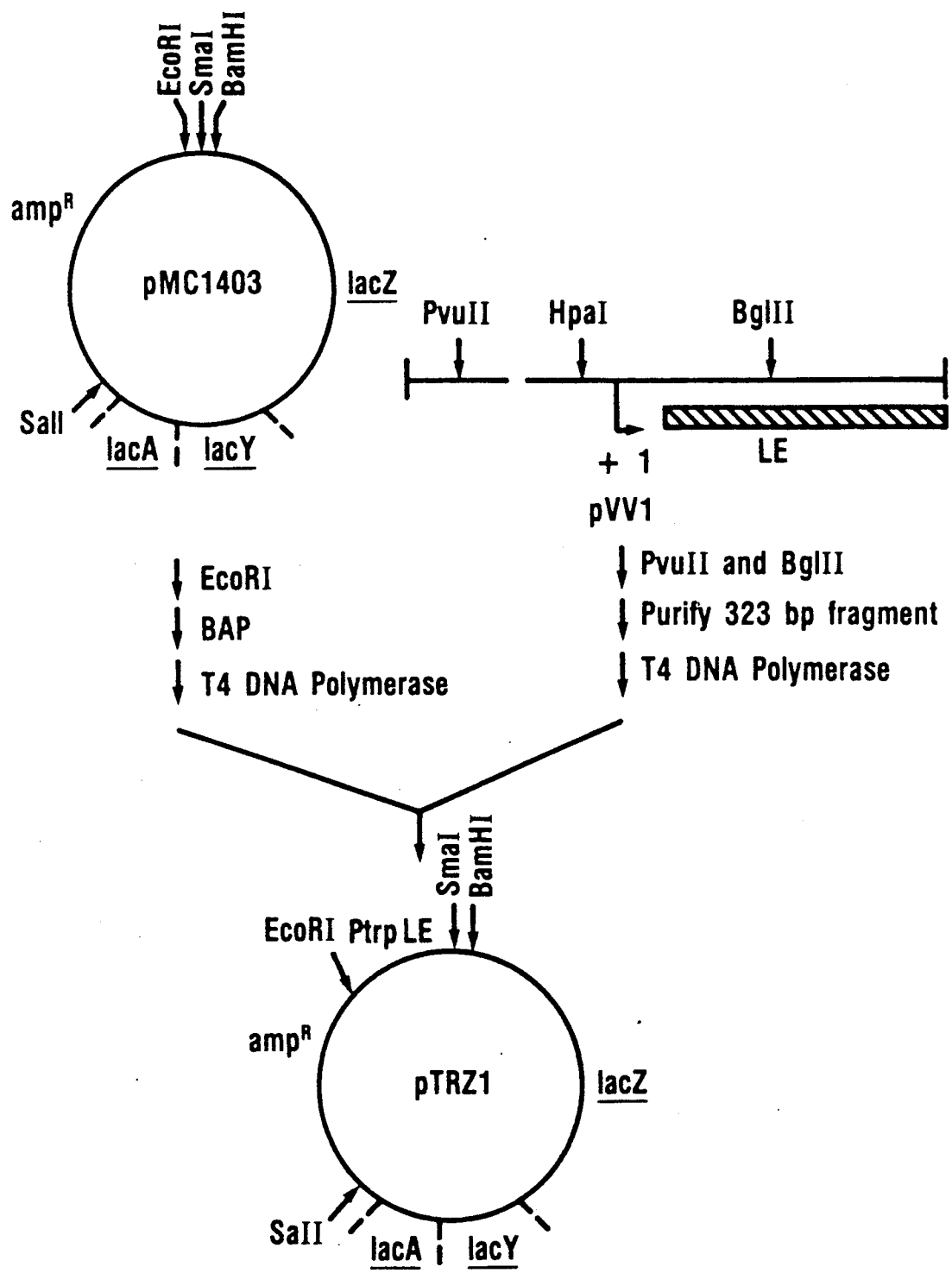
Figure 4. Construction of pTRZ1

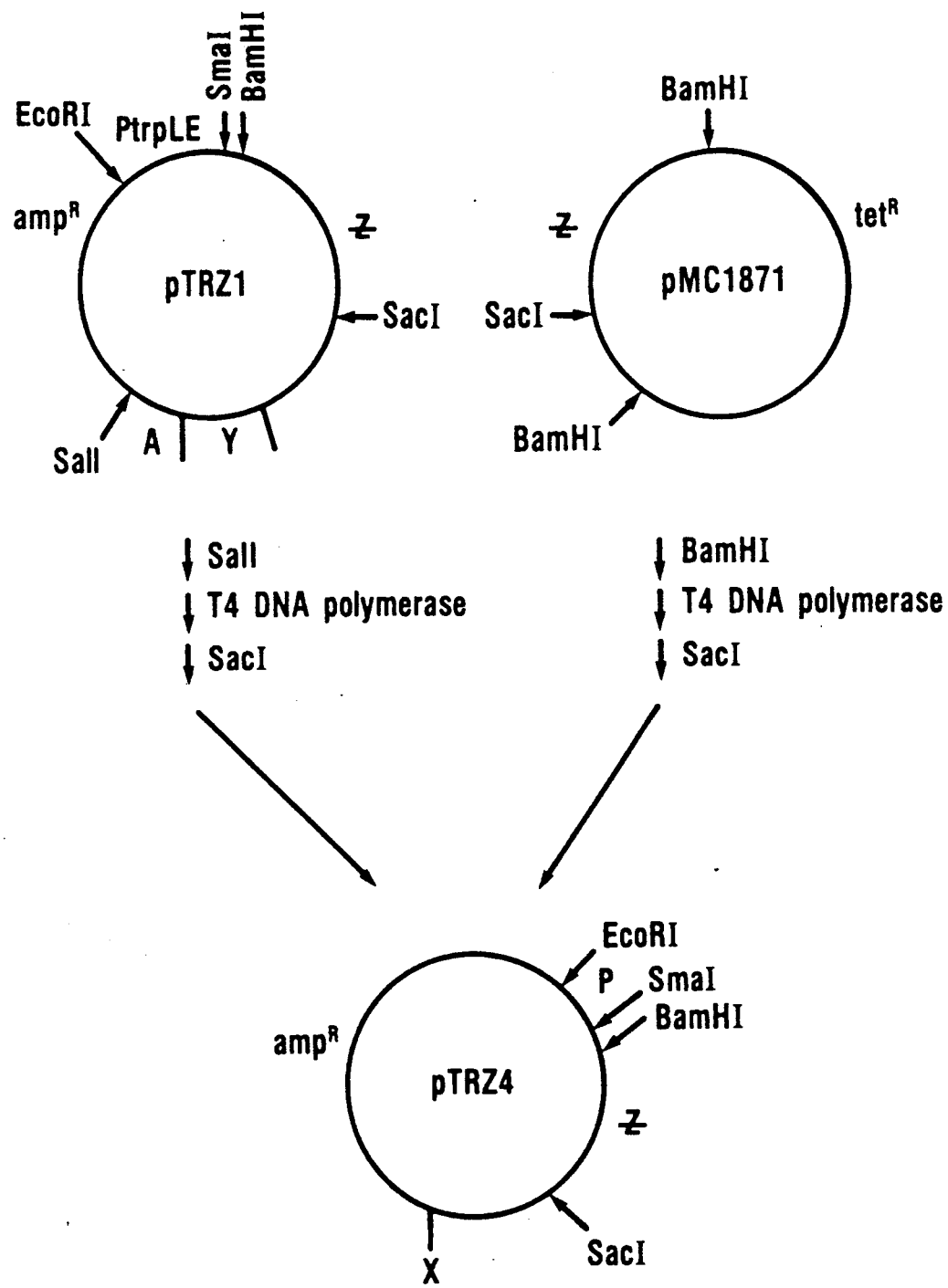
Figure 5. Construction of pTRZ4

PSEUDORABIES VIRUS (PRV) GENE, HOST CELL, METHOD FOR DETECTING ANIMALS INFECTED WITH PSEUDORABIES VIRUS, AND KIT THEREFOR

BACKGROUND OF THE INVENTION

The present patent application is a continuation-in-part of co-pending patent applications Ser. Nos. 606,103, filed May 2, 1984, now abandoned, and 606,307, filed May 2, 1984 now abandoned.

Pseudorabies virus (PRV) is a herpesvirus which can infect most domestic animals to cause clinical symptoms ranging from vomiting, diarrhea, fever, respiratory problems, neurological disorders, abortion, and culminating, generally, in death to the host animal.

Pseudorabies is known as Aujeszky's disease, mad itch and bulbar paralysis. When PRV infects pigs, a serious economic loss is incurred by the farmer. Very young pigs die whereas older pigs get sick and lose weight. Pregnant sows will abort when infected with PRV. Thus, an effective program for the eradication of PRV in swine is urgently needed.

Herpesviruses are among the most complex of animal viruses, coding for the synthesis of at least 50 virus specific proteins. Among the most immunologically reactive proteins of herpesviruses are the glycoproteins found in virion membranes and in the membranes of infected cells. The literature on pseudorabies glycoproteins (Ben-Porat, T., and Kaplan, A. S. Virology 41, 265-273, 1970; Kaplan, A. S., and Ben-Porat, T., Proc. Natl. Acad. Sci. USA, 66, 799-806, 1970) indicates that there are at least four viral glycoproteins in infected cells and virions.

Glycoproteins excreted into the medium have been reported for several herpesviruses, including herpes simplex virus (Kaplan, A. S., Erickson, J. S., and Ben-Porat, T., Prog. Med. Virol. 21, 1-12, 1975); herpes saimiri virus (Randall, R. E., and Honess, R. W., J. Gen. Virol. 51, 445-449, 1980); Marek's disease virus (Van Zaane, D., Brinkhof, J. M., Westenbrink, F., and Gielkens, A. L., Virology 121, 116-132, 1981); and pseudorabies virus (Erickson, J. S., and Kaplan, A. S., Virology 55, 94-102, 1973). In each of these cases except PRV, the excreted glycoprotein(s) is reported to be a subset of the virion glycoproteins. The publication by Ben-Porat and Kaplan, 1970, discloses that the PRV excreted glycoprotein is distinct from virion glycoproteins. This glycoprotein is known as 3a in the prior art (see Erickson and Kaplan, 1973, supra) and is referred to hereinafter as glycoprotein gX. Glycoprotein gX has the following characteristics when harvested from PRV-infected cells:

(1) it is the predominant protein in the culture medium of PRV infected animal cells in culture;
(2) it is a glycoprotein;
(3) it has a molecular weight of about 95 kilodaltons by standard SDS polyacrylamide gel electrophoresis (DATD cross-linked gel);
(4) it is a sulfated protein;
(5) it is soluble in about 1% perchloric acid;
(6) it is immunogenic in standard laboratory mice; and,
(7) it raises an immune response in the animal host which response is protective against a lethal challenge by a virulent strain of PRV.

We have isolated and mapped from the unique small region of pseudorabies virus (PRV) genome the gene encoding the PRV excreted glycoprotein gX and cloned said gene to express a fragment of the protein.

DESCRIPTION OF FIGURES AND CHARTS

FIG. 3 depicts the construction of the plasmid p60-11.

FIG. 4 depicts the construction of plasmid pTRZ1.

FIG. 5 depicts the construction of plasmid pTRZ4.

Charts 1A, 1B and 1C depict the base sequence of the gX gene.

Charts 2A, 2B and 2C depict the amino acid sequence of the gX protein.

SUMMARY OF THE INVENTION

The present invention provides a host cell transformed with a recombinant DNA molecule or a sequence of DNA basepairs comprising a DNA sequence of DNA basepairs encoding the PRV glycoprotein gX and fragments thereof and functional equivalents thereof.

More particularly the present invention provides a host cell transformed with a recombinant DNA molecule or a sequence of DNA basepairs comprising a DNA sequence of the formula set forth in Charts 1A, 1B and 1C hereof and fragments thereof and functional equivalents of said molecule and said fragments.

The present invention also provides a polypeptide expressed by a host transformed with a recombinant DNA molecule comprising a DNA sequence of the formula set forth in Charts 1A, 1B and 1C hereof and immunogenic fragments thereof and functional equivalents of said polypeptide and said immunogenic fragments.

More particularly the present invention provides a polypeptide having the formula set forth in Chart 2 and immunogenic fragments thereof and functional equivalents thereof.

The present invention also provides a recombinant sequence of DNA basepairs comprising DNA basepairs encoding the pseudorabies virus glycoprotein gX or immunogenic fragments thereof.

DETAILED DESCRIPTION OF INVENTION

The location of the gene encoding the major excreted glycoprotein of PRV, i.e., gX, was mapped using hybrid selection/translation experiments and restriction endonuclease analysis of subclones of PRV DNA fragments.

We cloned XH01 restriction fragments of PRV DNA (PRV rice strain) into a plasmid that contains a unique XH01 site to give the plasmid pUC1129. Hybridization of cytoplasmic RNA from PRV infected cells followed by translation in vitro to determine that the hybridized m-RNA coded for the gX protein was performed. pUC1129 is available from *Escherichia coli* HB101, NRRL B-15772. This biologically pure culture is available from the permanent collection of the Northern Regional Research Center Fermentation Laboratory (NRRL), U.S. Department of Agriculture, in Peoria, Ill., U.S.A.

Figure 1:
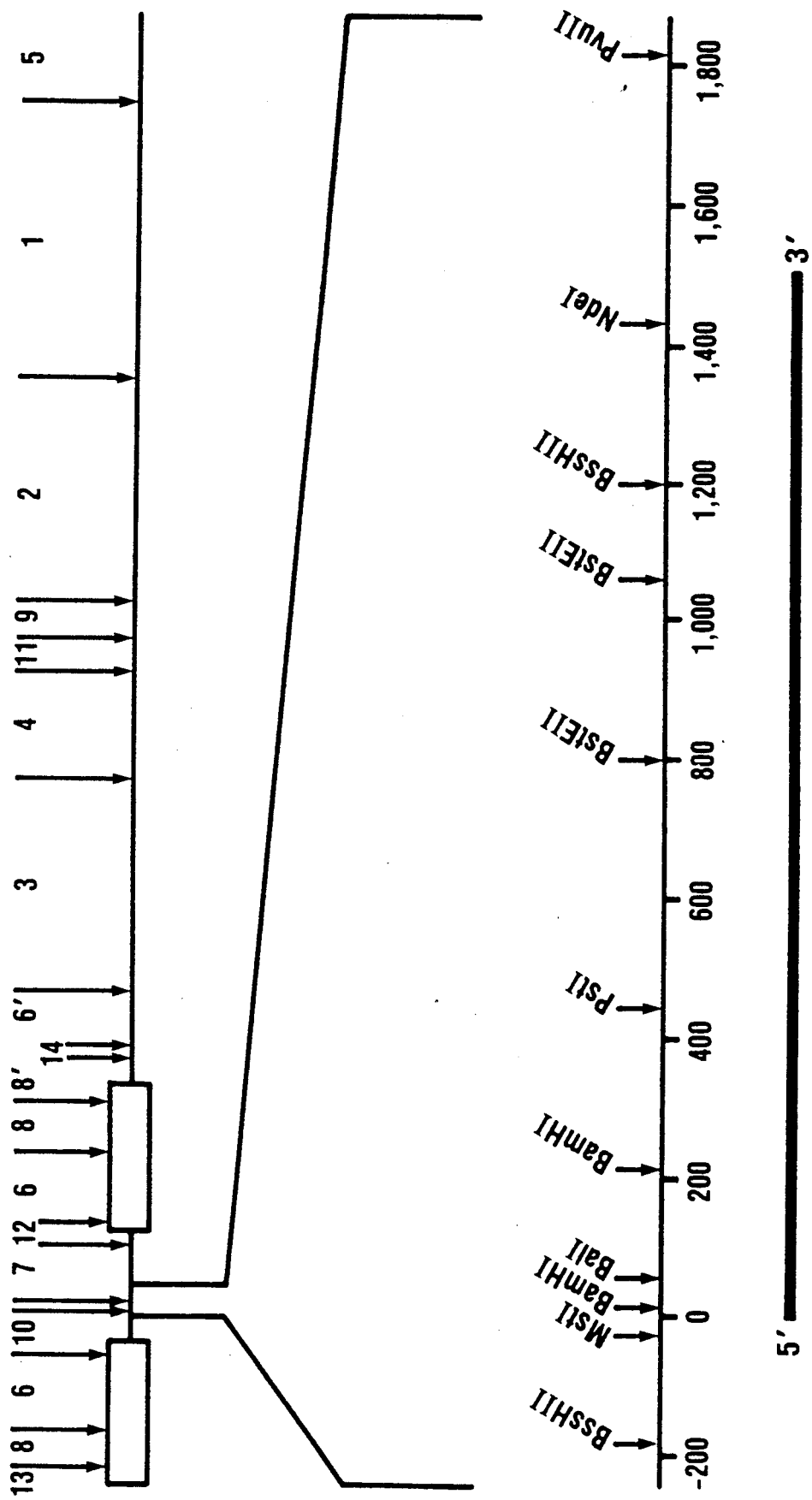
FIG. 1 depicts the BamHI restriction sites of the PRV genome with an enlargement of the region wherein the gX gene is located. The gX gene region is identified by the dark bar line (5'-3') with relevant restriction sites identified.
Figure 2:
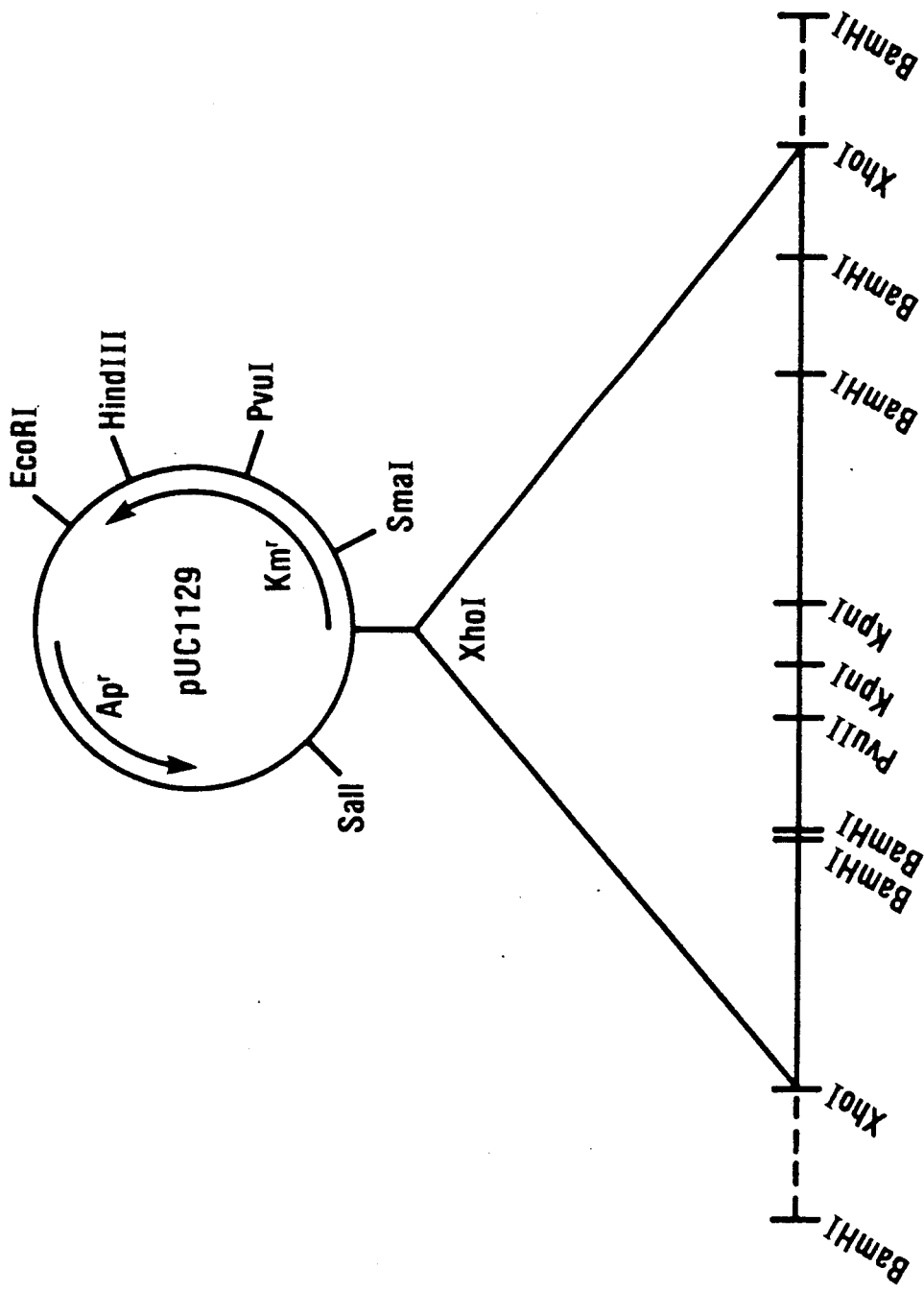
FIG. 2 depicts the structure of pUC1129 and details of the region wherein the gX gene is located.

*E. coli* HB101 containing pUC1129 can be grown up in L-broth by well known procedures. Typically the culture is grown to an optical density of 0.6 after which chloramphenicol is added and the culture is left to shake overnight. The culture is then lysed by, e.g., using high salt SDS and the supernatant is subjected to a cesium bromide/ethidium bromide equilibrium density gradient centrifugation to give the plasmids.

pUC1129 (FIG. 2) provides a source for the gene encoding the PRV glycoprotein gX. The availability of the gene sequence permits direct manipulation of the gene structure which concomitantly affects regulation of expression and/or the structure of the protein encoded by the gene. Now that the gX gene map is known, it is possible to clone the gene or portions thereof from any strain of PRV using this sequence as a hybridization probe, and express the entire gX protein or fragments thereof by recombinant techniques generally known in the art. Knowledge of the gX gene sequence enables us to deduce the amino acid sequence of the gX protein, and hence, the polypeptide may be produced by chemical synthesis as well as recombinant DNA techniques.

The primary structure (sequence) of the gene coding for gX and flanking regions of the DNA (5' and 3') is set forth in Charts 1A, 1B and 1C. The gene contains regulatory elements similar to those flanking most eucaryotic genes (e.g., promoter region, TATA box, appropriate initiation and termination codons marginating a large open reading frame, and polyadenylation signal(s)) and inferred from the sequence of the structural region of the gene structures like those expected in an excreted protein (e.g., signal sequence). The gene is relatively GC rich as is the entire PRV genome. The codon utilization of the gene reflects this abundance of G and C nucleotides. There are several interesting symmetries observed in the DNA sequence of which the most remarkable is a direct repeat of 50 basepairs with 100% homology. The repeat appears about 50% longer if one considers conservation of amino acid residues. An additional unusual feature is the presence of several "homopolyamino" acid segments in the protein (11-13 residues in length). The total length of the region of the PRV genome we have sequenced is greater than 2000 basepairs. The length of the open reading frame (from ATG to UGA) is 1497 nucleotides (>71% GC).

The gX gene or fragments thereof can be extracted from pUC1129 by digesting the plasmid DNA from a culture of NRRL B-15772 with appropriate endonuclease restriction enzymes, most suitably enzymes which will cleave at the sites of the gene depicted in FIG. 1. The restriction endonucleases are commercially available and their use is well known in the art and usually is provided by the commercial supplier of the enzyme. For example, as described in more detail hereinbelow, the fragment BamHI/PvuII was isolated by digestion of a preparation of pUC1129 with BamHI and PvuII, and isolation by gel electrophoresis.

The excised gene segment(s) can be ligated to various cloning vehicles or vectors for use in transforming a host cell. The vector may be a replicating vector, i.e., a vector which replicates within the host cell, or an integrating vector, i.e., a vector which serves to transport the exogenous gene material into the host cell and integrate said gene material with the DNA of the host cell. The vector contains heterologous gene sequences to initiate transcription and translation of the gX gene which are compatible with the host cell to be transformed. When the host cell is higher animal cell, e.g., a mammalian cell, the naturally occurring transcription and translation gene sequence of the gX can be employed or the naturally occurring translation gene sequence can be employed along with a heterologous promoter sequence. The vectors additionally contain a marker to provide a phenotypic trait used in selection of the transformed host cells. Additionally a replicating vector will contain a replicon. Typical vectors are plasmids and phages. In essence, one can use any DNA sequence that is capable of transforming a host cell such that said host cell is rendered capable of expressing the gX protein or portions thereof. Thus the present invention provides as a novel entity a sequence of DNA comprising basepairs encoding the PRV glycoprotein gX. By basepairs is meant the textbook definition of adenine (A) and thymine (T), and cytosine (C) and guanine (G) as occurs in DNA sequences.

The term host cell as used herein means a cell transformed with the gX gene and thus rendered capable of expressing the gX protein. The host cell can be procaryotic or eucaryotic. Illustrative procaryotic cells are bacterial microorganisms such as *E. coli, B. subtilis, Pseudomonas*, and *B. stearothermophilus*. Illustrative of eucaryotic cells are yeast, such as *Saccharomyces cerevisiae* (baker's yeast) or higher animal cells such as cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS-7 or MDCK cell lines.

As indicated above the vector, e.g., a plasmid, which is used to transform the host cell contains a gene sequence to initiate the transcription and translation of the gX gene sequence. When the host cells are bacterial microorganisms illustrative useful transcription and translation gene sequences are obtained from the trp promoter (Goeddel, et al., Nucleic Acids Res. 8, 4057 (1980)); the lac promoter (Chang, et al., Nature 275, 615 (1978)); the outer membrane protein promoter (EMBO J. 1, 771-775 (1982)); the bacteriophage λ promoter (Nucleic Acids Research 11, 4677-4688 (1983)) or the α-amylase (*B. subtilis*) promoter. When the host cell is yeast illustrative useful transcription and translation gene sequences are obtained from, e.g., α-mating factor. When the host cell is of insect or mammalian origin illustrative useful transcription and translation gene sequences are obtained from the SV-40 promoter (Science 222, 524-527 (1983)) or e.g., the metallothionein promoter (Nature 296, 39-42 (1982)). As noted above, when the host cell is mammalian, one may use the transcription and translation gene sequence for the gX gene but preferably in combination with a heterologous transcription initiation site. The plasmid or replicating or integrating DNA material containing the transcription or translation gene sequence is cleaved using restriction enzymes and adjusted in size as necessary or as desirable and ligated with the gX gene or fragments thereof by means well known in the art. When yeast or higher animal host cells are employed, terminator sequences from known yeast or mammalian genes are incorporated into the vector. Additionally, gene sequences to control replication of the host cell may be incorporated into the vector.

The host cells are competent or rendered competent for transformation by various means. When bacterial cells are the host cell they can be rendered competent by treatment with salts, typically a calcium salt, as generally described by Cohen, PNAS 69, 2110 (1972). A yeast host cell generally is rendered competent by removal of its cell wall or by other means such as ionic treatment (J. Bacteriol. 153, 163–168 (1983)). There are several well-known methods of introducing DNA into animal cells. These include: calcium phosphate precipitation, fusion of the recipient cells with bacterial protoplasts containing the DNA, treatment of the recipient cells with liposomes containing the DNA, and microinjection of the DNA directly into the cells.

The transformed cells are grown up by means well known in the art (Molecular Cloning, Maniatis, T., et al., Cold Spring Harbor Laboratory, 1982; Biochemical Methods in Cell Culture and Virology by Kuchler, R. J., Dowden, Hutchinson and Ross, Inc., 1977; Methods in Yeast Genetics by Sherman, F., et al., Cold Spring Harbor Laboratory, 1982) and the expressed gX protein is harvested from the cell medium in those systems where the protein is excreted from the host cell or from the cell suspension after disruption of the host cell system by, e.g., mechanical or enzymatic means which are well known in the art.

As described in detail in the specific Examples, the identity of the expressed gX protein was confirmed by immunoprecipitating labeled gX protein sera from mice injected with the protein.

As noted above the amino acid sequence of the gX protein as deduced from the gX gene structure is set forth in Chart 2. Immunological fragments of the gX protein are any portions of the polypeptide sequence which are capable of eliciting an immune response in an animal such as a mammal which has been injected with the polypeptide sequence. Illustrative examples of portions of the gX protein which are immunological fragments thereof are the following which are represented along with the DNA fragment coding for the polypeptide. In the codon the letter N represents adenine, thymine, cytosine or guanine; Q represents cytosine or thymine; and P represents guanine or adenine.

Formula I

```
                    5                       10
Pro Val His Asp Asp Arg Arg Pro Val Gly
CCN GTN CAQ GAQ GAQ CGN CGN CCN GTN GGN
                    AGP AGP
```

Formula II

```
                5                        10
Ala Gly Asp His Gln Arg Trp Arg Gly Cys Phe
GCN GGN GAQ CAQ CAP CGN TGG CGN GGN TGQ TTQ
                    AGP     AGP
```

Formula III

```
                    5                   10
Arg Ser Glu Ser Asp Asp Glu Val Val His
CGN TCN GAP TCN CAQ GAQ GAP GTN GTN CAQ
AGP AGQ     AGQ
```

Formula IV

```
                    5                       10
Ala Pro Glu Ala Pro Glu Glu Glu Glu Val Thr
GCN CCN GAP GCN CCN GAP GGN GAP GAP GTN ACN

15
Glu Glu Glu Ala Glu Leu
GAP GAP GAP GCN GAP CTN
                    TTP
```

-continued

Formula V

```
                    5                       10
Pro Ala Thr Glu Glu Gly Arg Gly Ala Glu Glu
CCN GCN ACN GAP GAP GGN CGN GGN GCN GAP GAP
                        AGP

15
Asp Glu Glu Leu Thr Ser
GAQ GAP GAP CTN ACN TCN
            TTP     AGQ
```

Formula VI

```
                    5                       10
Arg Pro His Pro Arg Gly Arg Asp His Asp His
CGN CCN CAQ CCN CGN GGN CGN GAQ CAQ GAQ CAQ
AGP             AGP     AGP 15                  20
Asp His Gly His His Arg Ala Asp Asp Arg
GAQ CAQ GGN CAQ CAQ CGN GCN GAQ GAQ CGN
                    AGP             AGP

25
Gly Pro Gln Arg His His Arg
GGN CCN CAP CGN CAQ CAQ CGN
            AGP         AGP
```

Formula VII

```
                    5                       10
His Val Arg Glu Ala Gln Gln Lys Ser Arg His
CAQ GTN CGM GAP GCM CAP CAP AAP TCN CGN CAQ
        AGP                     AGQ AGP

Ile Arg
ATQ CGN
ATA AGP
```

As indicated hereinabove the entire gene coding for the gX protein can be employed in constructing the vectors and transforming the host cells to express the gX protein or fragments of the gene coding for the gX protein can be employed whereby the resulting host cell will express portions or fragments of the gX protein. Examples of fragments of the gX gene which can be employed are set forth above with the polypeptide encoded thereby. Any fragment of the gX gene can be employed which results in the expression of a polypeptide which is an immunogenic fragment of the gX protein.

The following examples illustrates the present invention whereby the host cell, *E. coli* is transformed with a plasmid p60-11; however, it will be readily apparent to one skilled in the art that a variety of vectors could be constructed which would be suitable for transforming a host cell rendering it capable of expressing the gX protein. The recombinant DNA methods employed in practicing the present invention are standard procedures described in detail in Molecular Cloning, T. Maniatis, et al., Cold Spring Harbor Laboratory, 1982. Other references detailing techniques applicable in practicing the present invention include European patent application Nos. 093,619 and 032,134.

EXAMPLE 1

(a) Construction of Plasmid p60-11 (see FIG. 3)

The plasmid pTRZ4 contains a strong promoter, the trp promoter, and the trpLE translation initiation site with 12 amino acids from trpLE. The vector also contains the lacZ gene, minus its translation initiation site, immediately downstream from but out of phase with the trpLE sequences. A unique SmaI restriction site between the trpLE and lacZ sequences allows insertion of DNA fragments. Expression of the lacZ sequences requires insertion of a fragment containing no termination codons in a phase that joins the trpLE and lacZ sequences in phase.

A 1.5 kilobase BamHI/PvuII fragment containing a portion of the gX gene was isolated from pUC1129. A random population of subfragments of the BamHI/PvuII fragment was generated by a varied time of digestion of the fragment with Bal31 nuclease. This entire population of random fragments was ligated into the SmaI site of pTRZ4, which is between the trpLE and lacZ sequences, and a lac minus *E. coli* was transformed with the ligation mixture. The transformants were plated on Xgal plates to screen for β-galactosidase expression. One of the darkest blue colonies was isolated to obtain the modified pTRZ4 plasmid which we named p60-11. The p60-11 plasmid was found to contain a BamHI/EcoRI fragment of approximately 900 basepairs, indicating an insertion of approximately 600 basepairs in the BamHI/EcoRI fragment of pTRZ4.

(b) Protein Synthesis Directed by p60-11

The overproduced protein from p60-11 was found to be in an aggregated, insoluble form inside the cells, and this property could be used to purify the protein. The *E. coli* strain carrying plasmid p60-11 was grown to stationary phase in L broth, and diluted 1:100 in M9+1% casamino acids to induce synthesis of the recombinant protein. When the optical density of the culture exceeded 1.0, the cells were harvested and resuspended in 50 mM Tris HCl, pH 7.6, 0.3M NaCl, 0.5 mM EDTA (5–10 ml/liter of culture). Egg white lysozyme (Sigma) was added to a concentration of 1 mg/ml, and the reaction incubated on ice for 15 minutes. Then NP40 was added to a final concentration of 0.2%, and incubation continued for an additional 15 minutes on ice. The extract was sonicated until no longer viscous, and then centrifuged at 10,000 rpm for 15 minutes in a Sorvall HB-4 rotor. The recombinant p60-11 protein was found almost entirely in the pellet.

When the protein in these cells was analyzed using a Coomassie blue-stained SDS electrophoresis gel, the most abundant protein in the cells was seen to be a protein of apparent molecular weight of approximately 170,000. This is consistent with a hybrid protein that would contain an N-terminal trpLE sequence, a PRV glycoprotein coding sequence, and most of the lacZ at the C-terminus.

(c) Purification of p60-11 Protein

The p60-11 protein was purified by electrophoresis (SDS/PAGE) using 9.25% polyacrylamide gels with DATD as generally described by Morse, L., et al., J. Virol. 26, 389–410, 1978. Preparative gels for isolation of the protein were 3.0 mm in thickness and contained a 120 mm lane along with a 7 mm marker lane. Two ml of a boiled p60-11 pellet in 10 ml SDS sample buffer (4% SDS, 10% 2-mercaptoethanol, 6.0% sucrose, 200 μg/ml bromphenol blue, 100 mM Tris-HCl, pH 7.0) was applied to the wide lane and electrophoresed. A vertical slice was made in the gel to contain both the marker lane and 10 mm of the preparative lane; this was placed into Coomassie stain for 1 hour, and the remainder of the gel was covered with plastic wrap and placed at 4° C. After destaining the strip for approximately 1 hour (or until it's size matched perfectly with the unstained gel), the appropriate 170 kilodalton band was sliced out by using the stained molecular weight standards and prep lane bands as a guide. The gel slice was chopped into small pieces and transferred into a 10 ml syringe. This syringe was connected by tubing to another syringe. Five ml of gel elution buffer (0.05% SDS/0.05M NH4 HCO3) was then added, and was carefully forced through each syringe to macerate the acrylamide as much as possible. The contents were finally placed into a capped 50 ml polypropylene tube, 5 ml of gel elution buffer added, and the parafilm-sealed tube was shaken for 6 hours at 37° C. To remove unwanted acrylamide, the material was applied to a 30 ml syringe stoppered with glass wool. The eluted protein was collected by precipitation with 9 volumes of acetone, resuspended in 10 mM Tris-saline (pH 7.0), reverified via SDS/PAGE analysis, and stored at −20° C.

(d) Animals and Immunizations

Female ICR mice (age 2–4 months) were injected subcutaneously and intraperitoneally with macerated acrylamide containing 50 μg p60-11 protein mixed 1:1 with complete Freund's adjuvant. After three weeks rest, 60–90 μg of acetone precipitated, solubilized fusion protein mixed 1:1 with incomplete Freund's adjuvant was injected intraperitoneally. This was repeated every 10 days over six week's time. Serum samples were collected prior to each of the last two intraperitoneal boosts.

(e) Immunoprecipitations

The IgG binding affinity of S. aureus Cowan I cells (Calbiochem or Bethesda Research Laboratories) was utilized to precipitate immune complexes. Staph cells were prewashed in Buffer A (150 mM NaCl, 5 mM EDTA, 0.1% Triton X-100, 0.5% Nonidet P-40, 50 mM Tris-HCl, pH 7.4), Buffer B (same except 0.05% Nonidet P-40), and resuspended in Buffer C (Buffer B plus 1 mg/ml ovalbumin). $^{14}$C-glucosamine-labeled infected cell polypeptides (ICP's) or $^{14}$C gX (i.e., the medium from $^{14}$C-glucosamine-labeled cells) served as antigen (see description below under Cells and Virus) and was preincubated 1:1 with washed staph cells at 4° C. The prepared antigen supernatant was carefully removed after ultracentrifugation at 35,000 rpm for 45 minutes in a SW 50.1 rotor (Beckman). Twenty μl of antiserum was then incubated with 125 μl of antigen for one hour at 4° C., followed by the addition of 200 μl washed staph and a similar incubation step. The staph-antibody-antigen mixtures were then microfuged and washed 3 times in RIPA/SDS buffer (150 mM NaCl, 1% Triton X-100, 0.1% SDS, 1 mg/ml ovalbumin, 10 mM Tris-HCl, pH 7.2) and the supernatant drained well. The final pellet was resuspended in 50 μl of 2X SDS sample buffer and boiled for one minute. Staph cells were then pelleted and the supernatants applied to a 9.25% polyacrylamide gel for electrophoresis. The gels were made 0.75 mm thick by the procedure of Morse, L., et al., supra, and the gels were run for 16 hours at 5 mA/mm thickness. Anti-p60-11 serum pool, non-immune mouse serum, and immune pig serum (from a PRV-recovered animal) were independently assayed for immunoprecipitation of $^{14}$C gX and $^{14}$C ICP antigens. Anti-p60-11 exclusively precipitates the gX antigen as compared to the controls. A similar band is immunoprecipitated by this serum in the $^{14}$C ICP experiment, along with a faintly immunoprecipitated glycoprotein of unknown identity at 61 kilodaltons. Both bands are precipitated by the immune pig serum.

(f) Cells and Virus

Cells used for virus propagation and protein production were African Green Monkey (*C. aethiops*) kidney cells (ATCC CCL81; =VERO). Cells were maintained in Dulbecco's modified Eagle's medium (GIBCO) supplemented with 100 units/ml penicillin, 100 )g/ml streptomycin, 10 mM HEPES (pH 7.4), 2 mM glutamine, and 10% fetal bovine serum (KC Biological). Primary rabbit kidney cells were grown in the same medium.

Pseudorabies virus was isolated from a natural outbreak of PRV in swine. Virus stocks were prepared by infecting either Vero or rabbit kidney cells at low multiplicity (F 0.01). Although no properties of PRV are known to be dependent upon the cell line in which the virus is grown, we note that the biochemical experiments were done with virus grown on Vero cells, and animal challenge experiments were done with virus grown on rabbit kidney cells.

Cells were infected with between 5 and 10 plaque forming units per cell in medium 199 (GIBCO) supplemented with 1% fetal bovine serum. At 4 hours post infection, $^{14}C$ glucosamine was added (10 $\mu C$ in 2.5 ml medium per 25 $cm^2$ flask of cells; New England Nuclear, 54.2 mC/mmole). At 12-16 hours post infection, the medium was removed from the culture and stored frozen at $-70°$.

ICP's were harvested by shaking the infected cells into the medium and subsequent centrifugation. The cells were washed in phosphate buffered saline (PBS) without magnesium or calcium, and then resuspended in PBS minus magnesium and calcium, plus 1% NP40, 0.5% sodium deoxycholate, 0.1% SDS, and 200 $\mu g/ml$ ovalbumin. Debris was removed from the lysed cells by centrifugation and the labeled ICP's were stored at $-80°$ C.

ICP's were labeled with $^{35}S$-methionine by the same procedure, except the label added at 4 hours post infection was $^{35}$-methionine (1.5 mCi in 7.5 ml medium per 75 $cm^2$ flask of cells) in 199 medium with 1/10 normal concentration of methionine.

The pTRZ4 plasmid was constructed as depicted in FIGS. 4 and 5. FIG. 4 shows the construction of pTRZ1 which contains the *E. coli* trp promoter and translational initiation region of the leader peptide and the *E. coli* lacZ gene missing a few N-terminal amino acids, which would still have $\beta$-galactosidase activity. These two elements are joined in the vector such that the lacZ sequences are out of phase with respect to the translation frame of the trp gene.

After insertion of DNA fragments between the trp and lacZ sequences of such a vector, screening for expression of the $\beta$-galactosidase activity will then allow identification of plasmids expressing a hybrid protein.

The lacZ gene minus the N-terminal eight amino acids was obtained from pMC1403 (M. J. Casadaban, et al., J. Bacteriol. 143, 971-980 (1980). This plasmid has three unique restriction enzyme cleavage sites. pMC1403 was cut with EcoRI, dephosphorylated with BAP, and the ends made blunt with T4 DNA polymerase. The plasmid used as a source of the trp promoter was pVV1 (B. P. Nichols and C. Yanofsky, Methods in Enzymology, eds. L. Grossman and K. Moldane, 101, 155-164, Academic Press, N.Y., 1983). pVV1 contains the trp operon, with a 952 basepair deletion ($\Delta LE1413$) fusing the trp leader peptide to the trpLE gene. A 323 basepair fragment was isolated by digestion of pVV1 with PvuII plus BglII and and the preparative agarose gel electrophoresis (FIG. 4). The BglII site was filled by T4 DNA polymerase. The fragment was then ligated into the vector to give pTRZ1.

The use of pTRZ1 in the construction of pTRZ4 is shown in FIG. 5.

The plasmid pMC1871 (S. K. Shapira, et al., Gene 25, 71-82 (1983)) was used as a source of the C-terminal end of the lacZ gene without the lacY gene. This new C-terminus of lacZ was joined at the SacI site of the lacZ gene of pTRZ1 deleting all lac sequences downstream from the SacI site of pTRZ1. The resulting plasmid, pTRZ4, has the out-of-phase trpLE-lacZ fusion from TRZ1, with no lacY or lacA sequences.

EXAMPLE 2

In this example we set forth the use of the gX (p60-11) polypeptide in a diagnostic test to detect animals infected with PRV. While we used an ELISA assay (A. Voller, et al., The Enzyme-Linked Immunosorbent Assay (ELISA). Dynatech Laboratories, London (1979)), other similar assays known to those skilled in the art may also be employed.

Radioiodination of p60-11 Protein

The iodinating agent, 1,3,4,6-tetrachloro-3$\alpha$,6$\alpha$-diphenylglycouril (TCDG) was coated on the surface of a glass vial by evaporating 200 $\mu l$ of a chloroform solution containing 1.0 mg TCDG/ml. Iodination proceeded by adding 200 $\mu l$ of 0.5M sodium phosphate (pH 8.9) to the vial followed by 10 $\mu l$ of $^{125}I$ (0.5 mCi). After mixing and a 30 second incubation, 10 $\mu l$ of the p60-11 protein was added to the vial (p60-11 protein was dissolved at 500 $\mu g/ml$ in 50 mM borate, 0.9% NaCl, pH 8.8). This mixture was mixed well and incubated for 45 seconds. Then the reaction mixture was chromatographed over Bio-Gel P-6 DG (Sigma Company, St. Louis, Mo.; 7 mm $\times$ 185 mm column) using the borate buffer containing 25 $\mu g$ p60-11 protein/ml. Eight-drop fractions were collected and the $^{125}I$ in each fraction was determined. The first radioactive fractions were assumed to contain the radioiodinated protein and these were saved for subsequent analysis and use.

ELISA Using the p60-11 Protein

The antigen solution was prepared by diluting the p60-11 protein to 20 $\mu g/ml$ in Voller's buffer (50 mM NaHCO$_3$, 0.03% NaN$_3$, adjusted to pH 9.6 with NaOH). This was filtered through a 0.45 micron sterilizing filter (Sartorius SM 165 55 K). If needed, the filtered solution was further diluted with Voller's buffer before use.

100 $\mu l$ of the p60-11 protein in Voller's buffer (concentration about 2 $\mu g/ml$) was added to each well of a 96 well plate (Costar 3590 EIA). Adsorption occurred during an overnight, room-temperature incubation. The wells were washed three times with 300 $\mu l$ of Dulbecco's PBS (8 g/l NaCl, 0.2 g/l KCl, 0.2 g/l KH$_2$PO$_4$, and 1.14 g/l Na$_2$HPO$_4$; resultant pH was 7.3-7.4). Unreacted sites on the plastic surface were neutralized during a 1 hour room-temperature incubation with 3% BSA in Dulbecco's PBS (200 $\mu l$ per well). A single wash of each well with 300 $\mu l$ of Dulbecco's PBS followed. Then the adsorbed antigen was reacted with antibodies in 100 $\mu l$ of diluted serum (obtained from pigs exposed to PRV) during a 1 hour room-temperature incubation. Unreacted antibodies were removed by three washes with Dulbecco's PBS (300 Ml/well). then 100 Ml of a 1/1000 dilution of Protein A-horseradish peroxidase conjugate (diluted in 50 mM Tris, 0.05% Tween-20, 1% BSA, 0.02% NaN$_3$, pH 8.0) was added to each well for a 1 hour, room-temperature incubation. Again, the wells were washed three times with Dulbecco's PBS (300 Ml/well). One hundred $\mu l$ of substrate solution was added to each well. This solution was prepared by adding 10 mg of o-phenylenediamine (previously dissolved in 0.5 ml CH₃OH) and 25 μl of 30% (w/v) H₂O₂ to 49.5 ml buffer (17 mM Citric acid, 65 mM phosphate and 0.01% merthiolate adjusted to pH 6.3 with NaOH). The enzyme reaction continued for 15 to 35 minutes at room-temperature before 100 μl of 4.5M H₂SO₄ was added to each well. Absorbance of the chromophore was measured at 492 nmeters using a Titertek Multiskan. The optimal assay included 1% BSA in the serum dilution buffer and preferably a serum dilution which yields an absorbance of 0.4 or less. With this technique the signal to noise ratio was about 25 and made the assay effective for determining that a serum sample is from an infected pig.

By using this method, it is also possible to distinguish between vaccinated and infected animals. For example, pigs vaccinated with a PRV vaccine virus which does not produce glycoprotein gX (see, e.g., copending U.S. Pat. application Ser. No. 760,130, filed July 29, 1985) can be distinguished from pigs infected with virulent PRV which do produce gX by serological testing employing the gX polypeptide and immunological fragments thereof. Likewise the polypeptides and methods of the present invention can also be use to distinguish between, for example, pigs vaccinated with a PRV subunit vaccine (see, e.g., copending U.S. Pat. application Ser. No. 784,787, filed Oct. 4, 1985) and infected pigs, in a similar manner.

The gX polypeptide or immunological fragment or fragments thereof used for these diagnostic purposes can be placed in a mercantile kit comprising multiple containers wherein one of the containers has therein the pseudorabies virus (PRV) glycoprotein gX or an immunological fragment or fragments thereof.

Chart 1A
Basepair sequence (1-600) of the gX gene

```
         10         20         30
ATGAAGTGGG CAACGTGGAT CCTCGCCCTC
TACTTCACCC GTTGCACCTA GGAGCGGGAG 40         50         60
GGGCTCCTCG TGGTCCGCAC CGTCGTGGCC
CCCGAGGAGC ACCAGGCGTG GCAGCACCGG 70         80         90
AGAGAGGCCC CTCGGGAGCT CTGCTACCGC
TCTCTCCGGG GAGCCCTCGA GACGATGCCG 100        110        120
CACCCCGTCC ACGACGACCG GCGGCCCGTC
GTGGGGCAGG TGCTGCTGGC CGCCGGGCAG 130        140        150
GGGCCCGCGA CCGACGCCCA GCCCGTGAAC
CCCGGGCGCT GGCTGCGGGT CGGGCACTTG 160        170        180
CCGCTCGCCC CCGCCAACGC CACCGGGACG
GGCGAGCGGG GGCGGTTGCG GTGGCCCTGC 190        200        210
CACTACTCTC GCGGCTGCGA GATGCGCCTC
CTGATGAGAG CGCCGACGCT CTACGCGGAG 220        230        240
CTGGATCCGC CTCTCGACGT ATCGTCCCGC
GACCTAGGCG GAGAGCTGCA TAGCAGGGCG 250        260        270
TCCTCGGACC CCGTCAACGT GACCGTCGCC
AGGAGCCTGG GGCAGTTGCA CTGGCAGCGG
```

Chart 1A
Basepair sequence (1-600) of the gX gene

```
        280        290        300
TGGTTCTTTG ACGGCGGCCA CTGCAAGGTG
ACCAAGAAAC TGCCGCCGGT GACGTTCCAC 310        320        330
CCCCTCGTCC ACCGCGAGTA CTACGGCTGC
GGGGAGCAGG TGGCGCTCAT GATGCCGACG 340        350        360
CCCGGGGACG CCATGCCCTC CGTCGAGACG
GGGCCCCTGC GGTACGGGAG GCAGCTCTGC 370        380        390
TGCACCGGCG GGTACTCGTA CACCCGCACG
ACGTGGCCGC CCATGAGCAT GTGGGCGTGC 400        410        420
CGCATCGACA CCCTGATGGA GTACGCCCTC
GCGTAGCTGT GGGACTACCT CATGCGGGAG 430        440        450
GTGAACGCCA GCCTCGTGCT GCAGCCCGGG
CACTTGCGGT CGGAGCACGA CGTCGGGCCC 460        470        480
CTGTACGACG CCGGCCTGTA CATCGTCGTG
GACATGCTGC GGCCGGACAT GTAGCAGCAC 490        500        510
CTCGTCTTTG GCGACGACGC CTACCTCGGC
GAGCAGAAAC CGCTGCTGCG GATGGAGCCG 520        530        540
ACCGTCTCCC TGTCGGTGGA GGCCAACCTG
TGGCAGAGGG ACAGCCACCT CCGGTTGGAC 550        560        570
GACTACCCCT GCGGCATGAA GCACGGGCTC
CTGATGGGGA CGCCGTACTT CGTGCCCGAG 580        590        600
ACGATCACCC GCCCCGGGGC CACCCTCCCA
TGCTAGTGGG CGGGGCCCCG GTGGGAGGGT
```

Chart 1B
Basepair sequence (601-1200) of the gX gene

```
        610        620        630
CCCATCGCCC CCACGGCCGG CGACCACCAG
GGGTAGCGGG GGTGCCGGCC GCTGGTGGTC 640        650        660
CGCTGGCGCG GGTGCTTCCC CTCGACCGAC
GCGACCGCGC CCACGAAGGG GAGCTGGCTG 670        680        690
GAGGGCGCCT GGGAGAACGT GACCGCCGCC
CTCCCGCGGA CCCTCTTGCA CTGGCGGCGG 700        710        720
GAGAAGGGCC TGTCCGACGA CTACGCCGAC
CTCTTCCCGG ACAGGCTGCT GATGCGGCTG 730        740        750
TACTACGACG TGCACATCTT CCGCTCGGAG
ATGATGCTGC ACGTGTAGAA GGCGAGCCTC 760        770        780
TCTGACGACG AGGTCGTCCA CGGCGATGCC
AGACTGCTGC TCCAGCAGGT GCCGCTACGG 790        800        810
CCCGAGGCCC CCGAGGGCGA GGAGGTGACC
GGGCTCCGGG GGCTCCCGCT CCTCCACTGG
```

Chart 1B
Basepair sequence (601-1200) of the gX gene

```
          820        830        840
GAGGAGGAGG CCGAGCTGAC CTCCAGCGAC
CTCCTCCTCC GGCTCGACTG GAGGTCGCTG 850        860        870
CTCGACAACA TCGAGATCGA GGTCGTGGGC
GAGCTGTTGT AGCTCTAGCT CCAGCACCCG 880        890        900
TCTCCCGCCG CTCCCGCCGA GGGCCCGGCG
AGAGGGCGGC GAGGGCGGCT CCCGGGCCGC 910        920        930
ACGGAGGAGG GGCGCGGGGC CGAGGAGGAC
TGCCTCCTCC CCGCGCCCCG GCTCCTCCTG 940        950        960
GAGGAGCTGA CCTCCAGCGA CCTCGACAAC
CTCCTCGACT GGAGGTCGCT GGAGCTGTTG 970        980        990
ATCGAGATCG AGGTCGTGGG CTCGCCGCGG
TAGCTCTAGC TCCAGCACCC GAGCGGCGCC 1000       1010       1020
CCGCCCGCTT CTTCGCCGCC TCCACCACCC
GGCGGGCGAA GAAGCGGCGG AGGTGGTGGG 1030       1040       1050
CCGCGCCCCC ACCCGCGCGG CCGAGATCAC
GGCGCGGGGG TGGGCGCGCC GGCTCTAGTG 1060       1070       1080
GACCATGACC ACGGTCACCA CCGTGCGGAC
CTGGTACTGG TGCCAGTGGT GGCACGCCTG 1090       1100       1110
GACCGAGGAC CCCAGCGGCA TCACCGACTG
CTGGCTCCTG GGGTCGCCGT AGTGGCTGAC 1120       1130       1140
CCGCCGGAGC CGACCTTCGT CTCGCCCTCT
GGCGGCCTCG GCTGGAAGCA GAGCGGGAGA 1150       1160       1170
GACATCTTCG TGACCCCCAC CGGCAGCCCC
CTGTAGAAGC ACTGGGGGTG GCCGTCGGGG 1180       1190       1200
GCCCTGCTCC TGGGCTTCCT GGGCAGCGCG
CGGGACGAGG ACCCGAAGGA CCCGTCGCGC
```

Chart 1C
Basepair sequence (1201-1450) of the gX gene

```
         1210       1220       1230
CTCGCCTCGC GCCCCCTGCA CCTGACGGCC
GAGCGGAGCG CGGGGGACGT GGACTGCCGG 1240       1250       1260
GGGGAGACGG CCCAGCACGT GCGCGAGGCC
CCCCTCTGCC GGGTCGTGCA CGCGCTCCGG 1270       1280       1290
CAGCAGAAGA GCCGCCACAT CCGCTCCCTC
GTCGTCTTCT CGGCGGTGTA GGCGAGGGAG 1300       1310       1320
GGCGGCCTCC AGCTCTCGGT CGAGACCGAG
CCGCCGGAGG TCGAGAGCCA GCTCTGGCTC 1330       1340       1350
ACCACCAACA CCACCACCAC CCAGACGGGC
TGGTGGTTGT GGTGGTGGTG GGTCTGCCCG
```

Chart 1C
Basepair sequence (1201-1450) of th gX gene

```
         1360       1370       1380
CTGTCGGGCG ACATCCGCAC CTCGATCTAC
GACAGCCCGC TGTAGGCGTG GAGCTAGATG 1390       1400       1410
ATCTGCGTCG CCCTCGCCGG CCTGGTCGTC
TAGACGCAGC GGGAGCGGCC GGACCAGCAG 1420       1430       1440
GTGGGCATCG TCATCATGTG CCTCCATATG
CACCCGTAGC AGTAGTACAC GGAGGTATAC

1450
GCCATCATCA
CGCTAGTAGT
```

Chart 2A
Amino acid sequence (1-280) of gX protein

10
Met Lys Trp Ala Thr Trp Ile Leu Ala Leu Gly Leu Leu Val Val

20
Arg Thr Val Val Ala Arg Glu Ala Pro Arg Glu Leu Cys Tyr 30                               40
Gly His Pro Val His Asp Asp Arg Arg Pro Val Gly Pro Ala Thr

50
Asp Ala Gln Pro Val Asn Pro Leu Ala Pro Ala Asn Ala Thr Gly 60                               70
Thr Asp Tyr Ser Arg Gly Cys Glu Met Arg Leu Leu Asp Pro

80
Pro Leu Asp Val Ser Ser Arg Ser Ser Asp Pro Val Asn Val Thr 90                           100
Val Ala Trp Phe Phe Asp Gly Gly His Cys Lys Val Pro Leu Val

110
His Arg Glu Tyr Tyr Gly Cys Pro Gly Asp Ala Met Pro Ser Val 120                              130
Glu Thr Cys Thr Gly Gly Tyr Ser Tyr Thr Arg Thr Arg Ile Asp

140
Thr Leu Met Glu Tyr Ala Leu Val Asn Ala Ser Leu Val Leu 150                          160
Gln Pro Gly Leu Tyr Asp Ala Gly Leu Tyr Ile Val Val Leu Val

170
Phe Gly Asp Asp Ala Tyr Leu Gly Thr Val Ser Leu Ser Val Glu 180                          190
Ala Asn Leu Asp Tyr Pro Cys Gly Met Lys His Gly Leu Thr Ile

200
Thr Arg Pro Gly Ala Thr Leu Pro Pro Ile Ala Pro Thr Ala Gly 210                          220
Asp His Gln Arg Trp Arg Gly Cys Phe Pro Ser Thr Asp Glu

230
Gly Ala Trp Glu Asn Val Thr Ala Ala Glu Lys Gly Leu Ser 240                          250
Asp Asp Tyr Ala Asp Tyr Tyr Asp Val His Ile Phe Arg Ser Glu

260
Ser Asp Asp Glu Val Val His Gly Asp Ala Pro Glu Ala Pro Glu

270
Gly Glu Glu Val Thr Glu Glu Glu Ala Glu Leu Thr Ser Ser

Chart 2A
Amino acid sequence (1-280) of gX protein

280
Asp

Chart 2B
Amino acid sequence (281-498) of gX protein

290
Leu Asp Asn Ile Glu Ile Glu Val Val Gly Ser Pro Ala Ala Pro

300
Ala Glu Gly Pro Ala Thr Glu Glu Gly Arg Gly Ala Glu Glu 310 320
Asp Glu Glu Leu Thr Ser Ser Asp Leu Asp Asn Ile Glu Ile Glu

330
Val Val Gly Ser Pro Arg Pro Pro Ala Ser Ser Pro Pro Pro Pro 340 350
Pro Pro Arg Pro His Pro Arg Gly Arg Asp His Asp His Asp His

360
Gly His His Arg Ala Asp Asp Arg Gly Pro Gln Arg His His Arg 370 380
Leu Pro Pro Glu Pro Thr Phe Val Ser Pro Ser Asp Ile Phe Val

390
Thr Pro Thr Gly Ser Pro Ala Leu Leu Leu Gly Phe Leu Gly Ser 400 410
Ala Leu Ala Ser Arg Pro Leu His Leu Thr Ala Gly Glu Thr Ala

420
Gln His Val Arg Glu Ala Gln Gln Lys Ser Arg His Ile Arg Ser 430 440
Leu Gly Gly Leu Gln Leu Ser Val Glu Thr Glu Thr Thr Asn

450
Thr Thr Thr Thr Gln Thr Gly Leu Ser Gly Asp Ile Arg Thr Ser 460 470
Ile Tyr Ile Cys Val Ala Leu Ala Gly Leu Val Val Val Gly Ile

480
Val Ile Met Cys Leu His Met Ala Ile Ile Arg Ala Arg Ala Arg 490 498
Asn Asp Gly Tyr Arg His Val Ala Ser Ala

We claim:

1. A host cell transformed with a recombinant sequence of DNA basepairs comprising a sequence of DNA basepairs coding for the pseudorabies virus (PRV) glycoprotein gX or immunological fragments thereof.

2. A host cell of claim 1 wherein the sequence of DNA basepairs coding for the PRV glycoprotein gX or immunological fragment thereof has the following formula:

10 20 30
ATGAAGTGGG CAACGTGGAT CCTCGCCCTC
TACTTCACCC GTTGCACCTA GGAGCGGGAG 40 50 60
GGGCTCCTCG TGGTCCGCAC CGTCGTGGCC
CCCGAGGAGC ACCAGGCGTG GCAGCACCGG 70 80 90
AGAGAGGCCC CTCGGGAGCT CTGCTACCGC
TCTCTCCGGG GAGCCCTCGA GACGATGGCG

-continued 100 110 120
CACCCCGTCC ACGACGACCG GCGGCCCGTC
GTGGGGCAGG TGCTGCTGGC CGCCGGGCAG 130 140 150
GGGCCCGCGA CCGACGCCCA GCCCGTGAAC
CCCGGGCGCT GGCTGCGGGT CGGGCACTTG 160 170 180
CCGCTCGCCC CCGCCAACGC CACCGGGACG
GGCGAGCGGG GGCGGTTGCG GTGGCCCTGC 190 200 210
CACTACTCTC GCGGCTGCGA GATGCGCCTC
CTGATGAGAG CGCCGACGCT CTACGCGGAG 220 230 240
CTGGATCCGC CTCTCGACGT ATCGTCCCGC
GACCTAGGCG GAGAGCTGCA TAGCAGGGCG 250 260 270
TCCTCGGACC CCGTCAACGT GACCGTCGCC
AGGAGCCTGG GGCAGTTGCA CTGGCAGCGG 280 290 300
TGGTTCTTTG ACGGCGGCCA CTGCAAGGTG
ACCAAGAAAC TGCCGCCGGT GACGTTCCAC 310 320 330
CCCCTCGTCC ACCGCGAGTA CTACGGCTGC
GGGGAGCAGG TGGCGCTCAT GATGCCGACG 340 350 360
CCCGGGGACG CCATGCCCTC CGTCGAGACG
GGGCCCCTGC GGTACGGGAG GCAGCTCTGC 370 380 390
TGCACCGGCG GGTACTCGTA CACCCGCACG
ACGTGGCCGC CCATGAGCAT GTGGGCGTGC 400 410 420
CGCATCGACA CCCTGATGGA GTACGCCCTC
GCGTAGCTGT GGGACTACCT CATGCGGGAG 430 440 450
GTGAACGCCA GCCTCGTGCT GCAGCCCGGG
CACTTGCGGT CGGAGCACGA CGTCGGGCCC 460 470 480
CTGTACGACG CCGGCCTGTA CATCGTCGTG
GACATGCTGC GGCCGGACAT GTAGCAGCAC 490 500 510
CTCGTCTTTG GCGACGACGC CTACCTCGGC
GAGCAGAAAC CGCTGCTGCG GATGGAGCCG 520 530 540
ACCGTCTCCC TGTCGGTGGA GGCCAACCTG
TGGCAGAGGG ACAGCCACCT CCGGTTGGAC 550 560 570
GACTACCCCT GCGGCATGAA GCACGGGCTC
CTGATGGGGA CGCCGTACTT CGTGCCCGAG 580 590 600
ACGATCACCC GCCCCGGGGC CACCCTCCCA
TGCTAGTGGG CGGGGCCCCG GTGGGAGGGT 610 620 630
CCCATCGCCC CCACGGCCGG CGACCACCAG
GGGTAGCGGG GGTGCCGGCC GCTGGTGGTC 640 650 660
CGCTGGCGCG GGTGCTTCCC CTCGACCGAC
GCGACCGCGC CCACGAAGGG GAGCTGGCTG 670 680 690
GAGGGCGCCT GGGAGAACGT GACCGCCGCC
CTCCCGCGGA CCCTCTTGCA CTGGCGGCGG

```
            700         710         720
       GAGAAGGGCC TGTCCGACGA CTACGCCGAC
       CTCTTCCCGG ACAGGCTGCT GATGCGGCTG 730         740         750
       TACTACGACG TGCACATCTT CCGCTCGGAG
       ATGATGCTGC ACGTGTAGAA GGCGAGCCTC 760         770         780
       TCTGACGACG AGGTCGTCCA CGGCGATGCC
       AGACTGCTGC TCCAGCAGGT GCCGCTACGG 790         800         810
       CCCGAGGCCC CCGAGGGCGA GGAGGTGACC
       GGGCTCCGGG GGCTCCCGCT CCTCCACTGG 820         830         840
       GAGGAGGAGG CCGAGCTGAC CTCCAGCGAC
       CTCCTCCTCC GGCTCGACTG GAGGTCGCTG 850         860         870
       CTCGACAACA TCGAGATCGA GGTCGTGGGC
       GAGCTGTTGT AGCTCTAGCT CCAGCACCCG 880         890         900
       TCTCCCGCCG CTCCCGCCGA GGGCCCGGCG
       AGAGGGCGGC GAGGGCGGCT CCCGGGCCGC 910         920         930
       ACGGAGGAGG GGCGCGGGGC CGAGGAGGAC
       TGCCTCCTCC CCGCGCCCCG GCTCCTCCTG 940         950         960
       GAGGAGCTGA CCTCCAGCGA CCTCGACAAC
       CTCCTCGACT GGAGGTCGCT GGAGCTGTTG 970         980         990
       ATCGAGATCG AGGTCGTGGG CTCGCCGCGG
       TAGCTCTAGC TCCAGCACCC GAGCGGCGCC 1000        1010        1020
       CCGCCCGCTT CTTCGCCGCC TCCACCACCC
       GGCGGGCGAA GAAGCGGCGG AGGTGGTGGG 1030        1040        1050
       CCGCGCCCCC ACCCGCGCGG CCGAGATCAC
       GGCGCGGGGG TGGGCGCGCC GGCTCTAGTG 1060        1070        1080
       GACCATGACC ACGGTCACCA CCGTGCGGAC
       CTGGTACTGG TGCCAGTGGT GGCACGCCTG 1090        1100        1110
       GACCGAGGAC CCCAGCGGCA TCACCGACTG
       CTGGCTCCTG GGGTCGCCGT AGTGGCTGAC 1120        1130        1140
       CCGCCGGAGC CGACCTTCGT CTCGCCCTCT
       GGCGGCCTCG GCTGGAAGCA GAGCGGGAGA 1150        1160        1170
       GACATCTTCG TGACCCCCAC CGGCAGCCCC
       CTGTAGAAGC ACTGGGGGTG GCCGTCGGGG 1180        1190        1200
       GCCCTGCTCC TGGGCTTCCT GGGCAGCGCG
       CGGGACGAGG ACCCGAAGGA CCCGTCGCGC 1210        1220        1230
       CTCGCCTCGC GCCCCCTGCA CCTGACGGCC
       GAGCGGAGCG CGGGGGACGT GGACTGCCGG 1240        1250        1260
       GGGGAGACGG CCCAGCACGT GCGCGAGGCC
       CCCCTCTGCC GGGTCGTGCA CGCGCTCCGG 1270        1280        1290
       CAGCAGAAGA GCCGCCACAT CCGCTCCCTC
       GTCGTCTTCT CGGCGGTGTA GGCGAGGGAG 1300        1310        1320
       GGCGGCCTCC AGCTCTCGGT CGAGACCGAG
       CCGCCGGAGG TCGAGAGCCA GCTCTGGCTC 1330        1340        1350
       ACCACCAACA CCACCACCAC CCAGACGGGC
       TGGTGGTTGT GGTGGTGGTG GGTCTGCCCG 1360        1370        1380
       CTGTCGGGCG ACATCCGCAC CTCGATCTAC
       GACAGCCCGC TGTAGGCGTG GAGCTAGATG 1390        1400        1410
       ATCTGCGTCG CCCTCGCCGG CCTGGTCGTC
       TAGACGCAGC GGGAGCGGCC GGACCAGCAG 1420        1430        1440
       GTGGGCATCG TCATCATGTG CCTCCATATG
       CACCCGTAGC AGTAGTACAC GGAGGTATAC

1450
       GCCATCATCA
       CGCTAGTAGT
``` or a fragment thereof encoding an immunological fragment of glycoprotein gX or a functional equivalent of said sequence of DNA basepairs or fragment thereof.

3. A host cell of claim 2 which is a bacterial microorganism.

4. A host cell of claim 3 which is *E. coli.*

5. A host cell of claim 2 which is yeast.

6. A host cell of claim 2 which is an animal cell.

7. A host cell of claim 6 which is a mammalian cell.

8. In an immunological diagnostic method for detecting animals infected with pseudorabies virus comprising contacting serum from an animal of interest with antigen from pseudorabies virus and then detecting any antigen/antibody reaction, the improvement which comprises using as said antigen, pseudorabies virus glycoprotein gX antigen or immunological fragment(s) thereof, produced by a host cell of claim 1, and free from other pseudorabies virus antigens.

9. A diagnostic kit for performing the method according to claim 8, comprising pseudorabies virus glycoprotein gX or immunological fragment(s) thereof produced by a host cell transformed with a recombinant sequence of DNA basepairs comprising a sequence of DNA basepairs coding for the pseudorabies virus glycoprotein gX or immunological fragment(s) thereof and being free from other pseudorabies virus antigens.

10. A recombinant sequence of DNA basepairs comprising DNA basepairs encoding the pseudorabies virus (PRV) glycoprotein gX or an immunological fragment thereof.

11. A recombinant sequence of DNA basepairs of claim 10 wherein the DNA basepairs encoding the PRV glycoprotein gX has the formula:

```
            10          20          30
       ATGAAGTGGG CAACGTGGAT CCTCGCCCTC
       TACTTCACCC GTTGCACCTA GGAGCGGGAG 40          50          60
       GGGCTCCTCG TGGTCCGCAC CGTCGTGGCC
       CCCGAGGAGC ACCAGGCGTG GCAGCACCGG 70          80          90
       AGAGAGGCCC CTCGGGAGCT CTGCTACCGC
       TCTCTCCGGG GAGCCCTCGA GACGATGCCG 100         110         120
       CACCCCGTCC ACGACGACCG GCGGCCCGTC
       GTGGGGCAGG TGCTGCTGGC CGCCGGGCAG
```

```
         130        140        150
GGGCCCGCGA CCGACGCCCA GCCCGTGAAC
CCCGGGCGCT GGCTGCGGGT CGGGCACTTG 160        170        180
CCGCTCGCCC CCGCCAACGC CACCGGGACG
GGCGAGCGGG GGCGGTTGCG GTGGCCCTGC 190        200        210
CACTACTCTC GCGGCTGCGA GATGCGCCTC
CTGATGAGAG CGCCGACGCT CTACGCGGAG 220        230        240
CTGGATCCGC CTCTCGACGT ATCGTCCCGC
GACCTAGGCG GAGAGCTGCA TAGCAGGGCG 250        260        270
TCCTCGGACC CCGTCAACGT GACCGTCGCC
AGGAGCCTGG GGCAGTTGCA CTGGCAGCGG 280        290        300
TGGTTCTTTG ACGGCGGCCA CTGCAAGGTG
ACCAAGAAAC TGCCGCCGGT GACGTTCCAC 310        320        330
CCCCTCGTCC ACCGCGAGTA CTACGGCTGC
GGGGAGCAGG TGGCGCTCAT GATGCCGACG 340        350        360
CCCGGGGACG CCATGCCCTC CGTCGAGACG
GGGCCCCTGC GGTACGGGAG CAGCTCTGC 370        380        390
TGCACCGGCG GGTACTCGTA CACCCGCACG
ACGTGGCCGC CCATGAGCAT GTGGGCGTGC 400        410        420
CGCATCGACA CCCTGATGGA GTACGCCCTC
GCGTAGCTGT GGGACTACCT CATGCGGGAG 430        440        450
GTGAACGCCA GCCTCGTGCT GCAGCCCGGG
CACTTGCGGT CGGAGCACGA CGTCGGGCCC 460        470        480
CTGTACGACG CCGGCCTGTA CATCGTCGTG
GACATGCTGC GGCCGGACAT GTAGCAGCAC 490        500        510
CTCGTCTTTG GCGACGACGC CTACCTCGGC
GAGCAGAAAC CGCTGCTGCG GATGGAGCCG 520        530        540
ACCGTCTCCC TGTCGGTGGA GGCCAACCTG
TGGCAGAGGG ACAGCCACCT CCGGTTGGAC 550        560        570
GACTACCCCT GCGGCATGAA GCACGGGCTC
CTGATGGGGA CGCCGTACTT CGTGCCCGAG 580        590        600
ACGATCACCC GCCCCGGGCC CACCCTCCCA
TGCTAGTGGG CGGGGCCCCG GTGGGAGGGT
         610        620        630
CCCATCGCCC CCACGGCCGG CGACCACCAG
GGGTAGCGGG GGTGCCGGCC GCTGGTGGTC 640        650        660
CGCTGGCGCG GGTGCTTCCC CTCGACCGAC
GCGACCGCGC CCACGAAGGG GAGCTGGCTG 670        680        690
GAGGGCGCCT GGGAGAACGT GACCGCCGCC
CTCCCGCGGA CCCTCTTGCA CTGGCGGCGG 700        710        720
GAGAAGGGCC TGTCCGACGA CTACGCCGAC
CTCTTCCCGG ACAGGCTGCT GATGCGGCTG 730        740        750
TACTACGACG TGCACATCTT CCGCTCGGAG
ATGATGCTGC ACGTGTAGAA GGCGAGCCTC 760        770        780
TCTGACGACG AGGTCGTCCA CGGCGATGCC
AGACTGCTGC TCCAGCAGGT GCCGCTACGG 790        800        810
CCCGAGGCCC CCGAGGGCGA GGAGGTGACC
GGGCTCCGGG GGCTCCCGCT CCTCCACTGG 820        830        840
GAGGAGGAGG CCGAGCTGAC CTCCAGCGAC
CTCCTCCTCC GGCTCGACTG GAGGTCGCTG 850        860        870
CTCGACAACA TCGAGATCGA GGTCGTGGGC
GAGCTGTTGT AGCTCTAGCT CCAGCACCCG 880        890        900
TCTCCCGCCG CTCCCGCCGA GGGCCCGGCG
AGAGGGCGGC GAGGGCGGCT CCCGGGCCGC 910        920        930
ACGGAGGAGG GGCGCGGGGC CGAGGAGGAC
TGCCTCCTCC CCGCGCCCCG GCTCCTCCTG 940        950        960
GAGGAGCTGA CCTCCAGCGA CCTCGACAAC
CTCCTCGACT GGAGGTCGCT GGAGCTGTTG 970        980        990
ATCGAGATCG AGGTCGTGGG CTCGCCGCGG
TAGCTCTAGC TCCAGCACCC GAGCGGCGCC 1000       1010       1020
CCGCCCGCTT CTTCGCCGCC TCCACCACCC
GGCGGGCGAA GAAGCGGCGG AGGTGGTGGG 1030       1040       1050
CCGCGCCCCC ACCCGCGCGG CCGAGATCAC
GGCGCGGGGG TGGGCGCGCC GGCTCTAGTG 1060       1070       1080
GACCATGACC ACGGTCACCA CCGTGCGGAC
CTGGTACTGG TGCCAGTGGT GGCACGCCTG 1090       1100       1110
GACCGAGGAC CCCAGCGGCA TCACCGACTG
CTGGCTCCTG GGGTCGCCGT AGTGGCTGAC 1120       1130       1140
CCGCCGGAGC CGACCTTCGT CTCGCCCTCT
GGCGGCCTCG GCTGGAAGCA GAGCGGGAGA 1150       1160       1170
GACATCTTCG TGACCCCCAC CGGCAGCCCC
CTGTAGAAGC ACTGGGGGTG GCCGTCGGGG 1180       1190       1200
GCCCTGCTCC TGGGCTTCCT GGGCAGCGCG
CGGGACGAGG ACCCGAAGGA CCCGTCGCGC 1210       1220       1230
CTCGCCTCGC GCCCCCTGCA CCTGACGGCC
GAGCGGAGCG CGGGGGACGT GGACTGCCGG 1240       1250       1260
GGGGAGACGG CCCAGCACGT GCGCGAGGCC
CCCCTCTGCC GGGTCGTGCA CGCGCTCCGG 1270       1280       1290
CAGCAGAAGA GCCGCCACAT CCGCTCCCTC
GTCGTCTTCT CGGCGGTGTA GGCGAGGGAG 1300       1310       1320
GGCGGCCTCC AGCTCTCGGT CGAGACCGAG
CCGCCGGAGG TCGAGAGCCA GCTCTGGCTC
```

-continued

```
      1330       1340       1350
ACCACCAACA CCACCACCAC CCAGACGGGC
TGGTGGTTGT GGTGGTGGTG GGTCTGCCCG 1360       1370       1380
CTGTCGGGCG ACATCCGCAC CTCGATCTAC
GACAGCCCGC TGTAGGCGTG GAGCTAGATG
```

-continued

```
      1390       1400       1410
ATCTGCGTCG CCCTCGCCGG CCTGGTCGTC
TAGACGCAGC GGGAGCGGCC GGACCAGCAG 1420       1430       1440
GTGGGCATCG TCATCATGTG CCTCCATATG
CACCCGTAGC AGTAGTACAC GGAGGTATAC

1450
GCCATCATCA
CGCTAGTAGT
```

\* \* \* \* \*